United States Patent [19]

Katre et al.

[11] Patent Number: 4,931,544

[45] Date of Patent: Jun. 5, 1990

[54] SUCCINYLATED INTERLEUKIN-2 FOR PHARMACEUTICAL COMPOSITIONS

[75] Inventors: Nandini Katre, El Cerrito; Michael J. Knauf, San Bruno, both of Calif.

[73] Assignee: Cetus Corporation, Emeryville, Calif.

[21] Appl. No.: 148,106

[22] Filed: Jan. 27, 1988

Related U.S. Application Data

[63] Continuation of Ser. No. 903,668, Sep. 4, 1986, abandoned.

[51] Int. Cl.$^5$ .................... C07K 13/00; C07K 17/00; A61K 9/52
[52] U.S. Cl. .................... 530/351; 530/350; 530/402; 530/403; 530/404; 530/405; 530/406; 530/408; 530/409; 530/410; 604/890.1; 604/891.1; 514/2; 514/8; 514/12; 514/21; 424/422; 424/443; 424/464; 424/85.1; 424/85.2
[58] Field of Search ............... 530/350, 351, 404, 405, 530/406, 402, 408, 409, 410; 604/890, 891; 514/2, 8, 12, 21; 424/422, 443, 464; 484/85.1, 85.2

[56] References Cited

U.S. PATENT DOCUMENTS

| | | | |
|---|---|---|---|
| 4,414,147 | 11/1983 | Klibanov et al. | 424/85 |
| 4,569,790 | 2/1986 | Koths et al. | 530/351 |
| 4,609,546 | 9/1986 | Hiratoni | 424/85 |
| 4,659,570 | 4/1987 | Jerons | 424/85 |
| 4,748,152 | 5/1988 | Miyata et al. | 514/2 |

FOREIGN PATENT DOCUMENTS

0154316 9/1985 European Pat. Off. .
0219979 4/1987 European Pat. Off. .

OTHER PUBLICATIONS

Holcenberg, J. S. et al., J. Biol. Chem., 250, 4165–4170 (1975).
Holcenberg, J. S. et al., Cancer Research, 39, 3145–3151 (1979).
Rulter, D. A. and Wade, R. Br. J. Exp. Path., 52, 610–614 (1971).
Kissel et al., CA vol. 104, 1986, #397654.
Schwenke et al., (Biosis abst) #72037768 Feb. 25, 1981, pp. 201–212.
Murchmore et al., CA. vol. 106(25)#212268, 1987.
Jon et al., J. Immunol Method 42, 1981, pp. 79–92.
Coon et al., *J. Immunol* 114, 1975, pp. 1518–22.
Nilsson et al. CA vol. 104, 1986 #166832p.

*Primary Examiner*—Garnette D. Draper
*Attorney, Agent, or Firm*—Janet E. Hasak; Albert P. Halluin

[57] ABSTRACT

A pharmaceutical composition is prepared wherein biologically active conjugated interleukin-2 is dissolved in an aqueous carrier medium without the presence of a solubilizing agent. The unconjugated IL-2, which is not water soluble or not readily soluble in water at pH 6–8 without such solubilizing agent, is selectively conjugated to one or more succinyl groups by reaction with succinic anhydride.

20 Claims, No Drawings

SUCCINYLATED INTERLEUKIN-2 FOR PHARMACEUTICAL COMPOSITIONS

This application is a continuation of application Ser. No. 903 668 filed Sept. 4, 1986 now abandoned.

This invention relates to a chemical modification of biologically active interleukin-2 (IL-2) which alters the chemical and/or physiological properties of the IL-2. More specifically, this invention relates to selective succinylation of IL-2 to render it soluble at physiological pH.

Many heterologous proteins produced in microbial host cells, including IL-2, are found as insoluble material in refractile bodies. In addition, IL-2 is hydrophobic in nature and tends to stick to materials and to itself (i.e., aggregate) rather than remain in solution. Also, in recombinant IL-2 from *E. coli* is unglycosylated, whereas its native counterpart is a water-soluble, glycosylated molecule. Modification of the IL-2 which might alter its solubility properties would be desirable to facilitate formulation of IL-2 for therapeutic use. In addition, modifications may reduce or eliminate aggregation of the IL-2 when it is introduced in vivo, thereby reducing its immunogenicity.

The use of polypeptides such as IL-2 in circulatory systems for the purpose of producing a particular physiological response is well known in the medicinal arts. A limitation to the potential therapeutic benefit derived from the clinical use of polypeptides is their ability to elicit an immune response in the circulatory system. This immune response may be caused by aggregates in the material prior to injection as described by R. Illig (1970), *J. Clin. Endrocr.*, 31, 679–688, W. Moore (1978), *J. Clin. Endrocrinol. Metab.*, 46, 20–27 and W. Moore and P. Leppert (1980), *J. Clin. Endrocrinol. Metab.*, 51, 691–697.

Modification of these potentially useful therapeutic polypeptides so as to preclude or at least reduce an immune response while still maintaining desired physiological activities of the polypeptide would allow the use of these polypeptides in the mammalian circulatory system without the aforementioned disadvantages.

U.S. Pat. No. 4,179,337 discloses conjugating of water-soluble polypeptides such as enzymes and insulin to PEG or PPG. U.S. Pat. No. 4,002,531 discloses a different method of conjugating enzymes to PEG through an aldehyde derivative. Copending U.S. application Ser. No. 866,456 filed May 218 1986 now abandoned and refiled as U.S. Ser. No. 148,145, filed Jan. 25, 1988, now U.S. Pat. No. 4,766,106, issued Aug. 23, 1988 discloses conjugation of interferon-$\beta$, interleukin-2 or an immunotoxin with PEG or polyoxyethylated polyols to obtain increased solubility and reduced immunogenicity of the protein. Also, EP 154,316 published September 11, 1985 to Takeda Chemical Industries, Ltd., discloses and claims chemically modified lymphokines such as IL-2 containing PEG bonded directly to at least one primary amino group of a lymphokine. Copending U.S. application Ser. No. 879,456 filed June 27, 1986, now U.S. Pat. No. 4,745,180, issued May 17, 1988 (Cetus Docket 2292) discloses a process for solubilizing proteins by conjugating them to heparin fragments.

The properties of various succinylated proteins are described in Holcenberg, J.S. et al., *J. Biol. Chem.*, 250, 41654170 (1975) Holcenberg, J. S. et al., *Cancer Research*, 39, 3145–3151 (1979), and Rulter, D. A. and Wade, *Br. J. Exp. Path.*, 52, 610–614 (1971) None of these articles discusses any solubility changes in the protein as a result of succinylation.

U.S. Pat. No. 4,414,147 describes rendering interferon less hydrophobic by conjugating it to an anhydride of a dicarboxylic acid such as succinic anhydride. While the interferon-$\beta$ specifically exemplified therein is made less hydrophobic, it appears also to lose substantial specific activity upon succinylation.

It is not a priori possible to predict which selected proteins would be favorably responsive to derivatization with which chemical moieties due to the vast difference in the pharmacokinetics and physical properties of various proteins.

SUMMARY OF THE INVENTION

Accordingly, the present invention provides for succinylating interleukine-2, which is not ordinarily soluble in water under ambient conditions at pharmaceutically acceptable pH ranges, to render it soluble in aqueous buffer under such conditions. This succinylation also avoids addition to extraneous solubilizing additives such as detergents or denaturants to keep the protein in solution. The succinylated IL-2 retains the biological activity of the unmodified IL-2, both initially and over time. The in vivo half-life may be modulated by selecting appropriate conditions such as degree of succinylation.

More specifically, the present invention is directed to a biologically active conjugated interleukin-2 (IL-2) wherein the IL-2 is covalently and selectively conjugated to one or more succinyl moieties, and wherein said IL-2 in its unconjugated form is normally hydrophobic and not soluble in an aqueous carrier medium at pH 6–8 in the absence of a solubilizing agent.

The invention also provides a pharmaceutical composition comprising a non-toxic, inert, pharmaceutically acceptable aqueous carrier medium in which the succinylated IL-2 herein is dissolved.

Preferably the IL-2 is recombinant interleukin-2.

Another aspect of the invention resides in a process for preparing a biologically active, succinylated IL-2 comprising:

(a) reacting biologically active, normally hydrophobic, water-insoluble interleukin-2 with succinic anhydride, and (b) isolating the succinylated interleukin-2.

A further aspect relates to a process for preparing a pharmaceutical composition comprising the above two steps, followed by (c) formulating said succinylated interleukin-2 in a non-toxic, inert, pharmaceutically acceptable aqueous carrier medium.

In a final aspect, the invention herein provides a sustained release formulation, i.e., microencapsulated form, of the succinylated protein described above, which is useful for pharmaceutical treatment of animals for, e.g., shipping fever.

DESCRIPTION OF THE PREFERRED EMBODIMENTS

As used herein, the term "normally hydrophobic, water insoluble" as describing the interleukin-2 refers to those interleukin-2 molecules which are insoluble or not readily soluble in water or an aqueous medium under ambient conditions of room temperature and atmospheric pressure at a pH of between about 6 and 8, i.e., at about neutral or physiological pH. The modification herein acts to increase the solubility of such interleukin-2 proteins wherein they are subjected to such physiological conditions. For purposes herein, solubility may be tested by (1) turbidity, as measured by spectrophotometric means, (2) S value, as measured by ultracentrifugation, wherein the monomeric protein sedimentation rate rather than the much greater aggregate sedimentation rate signals solubility, and (3) apparent native molecular weight, as measured by size exlusion chromatography, wherein the soluble interleukin-2 is closer to this value the insoluble interleukin-2. The exact numbers which would indicate solubility for each of these tests will depend on the type of buffer in which the interleukin-2 is formulated, the pH of the buffer, and the ionic strength of the buffer.

The interleukin-2 herein may be obtained from tissue cultures or by recombinant techniques, and from any mammalian source such as, e.g., mouse, rat, rabbit, primate, pig, and human. Preferably, the interleukin-2 is derived from a human source, and more preferably is a recombinant, human protein.

The term "recombinant interleukin-2," designated as IL-2, preferably human IL-2, refers to interleukin-2 having comparable biological activity to native IL-2 prepared by recombinant DNA techniques as described, e.g., by Taniguchi et al., *Nature*, 302:305–310 (1983) and Devos, *Nucleic Acids Research*, 11:4307–4323 (1983). In general, the gene coding for IL-2 is excised from its native plasmid and inserted into a cloning vector to be cloned and then into an expression vector, which is used to transform a host organism, preferably a microogranism, and most preferably *E. coil*. The host organism expresses the foreign gene to produce IL-2 under expression conditions.

More preferably the IL-2 is a mutein as described in U.S. Pat. No. 4,518,584, in which the cysteine normally occurring at position 125 of the wild-type or native molecule has been replaced by a neutral amino acid such as serine or alanine. Alternatively or conjuctively, the IL-2 mutein may be one as described in copending U.S. application Ser. No. 810,656 filed December 17, 1985 now abandoned, and refiled as U.S. Ser. No. 893,186, filed Aug. 5, 1986, now U.S. Pat. No. 4,752,585, issued June 21, 1988, the disclosure of which is incorporated herein by reference, in which the methionine normally occurring at position 104 of the wild-type or native molecule has been replaced by a neutral amino acid such as alanine. Finally, the IL-2 employed may have one or more of the first five N-terminal amino acids of the native IL-2 deleted.

Preferably, the IL-2 is a protein produced by a microorgansium or by yeast which has been transformed with the human cDNA sequence of IL-2 which encodes a protein with an amino acid sequence at least substantially identical to the amino acid sequence of native human IL-2, including the disulfide bond of the cysteines at positions 58 and 105, and has biological activity which is common to native human IL-2. Substantial identity of amino acid sequences means the sequences are identical or differ by one or more amino acid alterations (additions, substitutions) which do not cause an adverse functional dissimilarity between the synthetic protein and native human IL-2. Examples of IL-2 proteins with such properties include those described by Taniguchi et al., supra; Devos, supra; European Patent Application Nos. 91,539 and 88,195; U.S. Pat. No. 4,518,584, supra, and U.S. Pat. No. 4,752,585 supra. Most preferably, the IL-2 is $ser_{125}IL-2$, des-$ala_1ser_1$-$_{25}IL-2$, des-$ala_1IL-2$, des-$ala_1ala_{104}IL-2$, or des-$ala_1ala_{10-4}ser_{125}IL-2$, where "des-$ala_1$" indicates that the N-terminal alanyl residue of the IL-2 has been deleted.

The precise chemical structure of the IL-2 herein will depend on a number of factors. As ionizable amino and carboxyl groups are present in the molecule, a particular IL-2 may be obtained as an acidic or basic salt, or in neutral form. All such preparations which retain their bioactivity when placed in suitable environmental conditions are included in the definition of IL-2 herein. Further, the primary amino acid sequence of the IL-2 may be augmented by derivatization using sugar moieties (glycosylation) or by other supplementary molecules such as lipids, phosphate, acetyl groups and the like, more commonly by conjugation with saccharides. Certain aspects of such augmentation are accomplished through post-translational processing systems of the producing host; other such modifications may be introduced in vitro. In any event, such modifications are included in the definition of IL-2 herein so long as the bioactivity of the IL-2 is not destroyed. It is expected, of course, that such modifications may quantitatively or qualitatively affect the bioactivity by either enhancing or diminishing the activity of the IL-2 in the various assays.

The hydrophobic recombinant IL-2 produced from transformed host cells containing recombinant DNA precipitates inside the cell as opposed to being soluble in the cell culture medium. The intracellularly produced IL-2 must be separated from the cellular debris and recovered from the cell before it can be formulated into a purified biologically active material. Commonly owned copending U.S. application Ser. No. 843,997 filed on March 25, 1986, now U.S. Pat. No. 4,748,234, issued May 31, 1988, entitled "Process for Recovering Refractile Bodies Containing Heterologous Proteins From Microbial Hosts" to W. Hanisch et al., the entire disclosure of which is incorporated herein by reference, discloses a process for isolating such a refractile material. In this process the cell membrane of the transformed host microoogranism is disrupted, greater than 99% by weight of the salts is removed from the disruptate, the desalted disruptate is redisrupted, a material, preferably a sugar such as sucrose, is added to the disruptate to create a density or viscosity gradient in the liquid within the disruptate, and the refractile material is separated from the cellular debris by high-speed centrifugation, i.e., at about 10,000 to 40,000 x g. Preferably, the salts are removed from the disruptate by diafiltration or centrifugation and sucrose is added to increase the density of the liquid to about 1.1 to 1.3 g/ml.

After the centrifugation step, the pellet containing the refractile bodies is solubilized with a denaturant such as sodium dodecyl sulfate, the resulting suspension is centrifuged, and the supernatant containing the protein is treated to isolate the protein. The protein is separated from the supernates by appropriate means such as reverse-phase high pressure liquid chromatography (RP-HPLC) and/or gel filtration chromatography. After such separation, the protein is preferably oxidized to ensure the production of high yields of recombinant protein in a configuration most like its native counterpart. Such oxidation is described in U.S. Pat. No. 4,530,787 to Z. Shaked et al., the disclosure of which is incorporated herein by reference. The oxidation may also be carried out by reacting an aqueous solution containing a solubilized form of the protein at a pH between about 5.5 and 9 in the presence of air with at least an effective amount of an oxidation promoter containing a $Cu^{+2}$ cation, as described in U.S. Pat. No. 4,572,798 to K. Koths et al., the disclosure of which is incorporated herein by reference. The preferred oxidation promoter or oxidant is $CuCl_2$ or (o-phenanthroline)$_2$ $Cu^{+2}$. After oxidation, the protein may optionally be desalted and purified further by RP-HPLC, dilution/diafiltration, S 200 gel filtration chromatography, and ultrafiltration techniques before succinylation as described further hereinbelow. The succinylation may be carried out, however, at any step after the heterologous IL-2 has been isolated in sufficiently pure form to be biologically active for therapeutic purposes. The point at which the modification will occur will depend on the ultimate purity of the IL-2 required for the final pharmaceutical formulation and use.

The term "selectively conjugated" as used herein to apply to the IL-2 refers to those IL-2 proteins which are covalently bonded via one or two of the amino acid residues of the protein, depending mainly on the reaction conditions and the ultimate use. While the residues may be any reactive amino acids on the IL-2, such as one or two cysteines or the N-terminal amino acid group, preferably the reactive amino acid is lysine, which is linked to the succinic anhydride through its free ε-amino group.

According to the process of this invention, the IL-2, which is normally hydrophobic and water insoluble, is rendered soluble in an aqueous carrier medium, preferably at a pH of about 5 to 8, more preferably about 6-8 and most preferably, 6.5-7.8, without use of solubilizing agents, by modifying the IL-2 through conjugation to succinyl moieties. If the IL-2 is reacted through its lysine residues, the pH of the reaction is preferably about 7 to 9, more preferably 8-9. The success of such a modification, including retention of substantial biological activity, cannot be predicted from earlier succinylation of interferon-β.

The succinyl moiety(ies) to which the IL-2 is attached is/are derived from succinic anhydride. The succinic anhydride selectively reacts with free amino or other reactive groups of the IL-2. It will be understood, however, that the total amount of succinic anhydride employed and the time for reaction, to obtain optimum results, will depend on the specific properties desired, to avoid having the succinic acic react with too many or too few particularly active groups on the IL-2. The exact amount of succinic anhydride employed depends on the solvent employed (an organic solvent may require less succinic anhydride), the protein concentration, the pH of the reaction medium, the salt present in the reaction medium, and the specific properties desired. It is preferred, however, to use at least 2 moles, more preferably from about 2 to 60 moles, of succinic anhydride per mole of IL-2. The final amount to be employed is a balance to maintain optimum activity and solubility (achieved using higher amounts of succinic anhydride), while at the same time optimizing, if possible, the half-line of the IL-2 (the half-life decreases with higher amounts of succinic anhydride). Preferably, at least about 50% of the biological activity of the IL-2 is retained, and most preferably 100% is retained. It is noted that while the monosubstituted succinyl-IL-2 has improved solubility without added solubilizers at pH 7, storage at 4° C. for three days or physical agitation at room temperature causes visible precipitation of the IL-2 protein.

The covalent succinylation reaction takes place by contacting the IL-2 with succinic anhydride, preferably at about pH 5-9, more preferably 7-9, and most preferably 8-9 if the reactive groups on the IL-2 are lysine groups. The reaction may take place in any solvent which will not adversely affect the protein. For example, dimethyl formamide may be employed if the protein is not affected adversely. Preferably, the reaction takes place at room temperature in an aqueous solution containing a buffer with a solubilizing agent such as sodium dodecyl sulfate.

The succinic acid may be added all at once to the solution of the IL-2, but preferably it is added at intervals of, e.g., five minutes as shown in the examples hereinbelow. The bioactivity of the succinylated IL-2 may be monitored at the various time points during the reaction.

After the reaction, the succinylated IL-2 is isolated from the reaction mixture. This may be accomplished by separating the IL-2 and succinylated IL-2 species from other species such as the solubilizing agent, and then, if the mono- or di-succinylated IL-2 is prepared, separating the IL-2 species such as by use of a TSK-DEAE ion exchange HPLC and desalting the separated IL-2 species. If more highly modified species are produced, after the solubilizing agent is removed, the pH may be lowered to neutral pH, if not done earlier, and the sample desalted and concentrated.

The IL-2 thus succinylated is then formulated in a non-toxic, inert, pharmaceutically acceptable aqueous carrier medium, preferably at a pH of about 3 to 8, more preferably 6-8. For in vitro applications, the modes of administration and formulation are not critical. Aqueous formulations compatible with the culture or perfusion medium will generally be used. When used in vivo for therapy, the sterile product will consist of a mixture of IL-2 dissolved in an aqueous buffer in an amount which will provide a pharmaceutically acceptable pH when the mixture is reconstituted. A water-soluble carrier such as mannitol may optionally be added to the medium. The currently formulated unmodified IL-2 is stable for at least six months at 4° C.

The dosage level of IL-2 in the formulation will depend on the in vivo efficacy data obtained after preclinical testing and will depend mainly on the ultimate use.

If the formulation is lyophilized, the lyophilized mixture may be reconstituted by injecting into the vial a conventional parenteral aqueous injection such as, e.g., distilled water.

The reconstituted formulation prepared as described above is suitable for parenteral administration to humans or other mammals in therapeutically effective amounts (i.e., amounts which eliminate or reduce the patient's pathological condition) to provide therapy thereto. IL-2 therapy is appropriate for a variety of immunomodulatory indications such as T cell mutagenesis, induction of cytotoxic T cells, augmentation of natural killer cell activity, induction of IFN-gamma, restoration or enhancement of cellular immunity (e.g., treatment of immune deficient conditions), and augmentation of cell medicated anti-tumor activity.

In an alternative to direct administration of IL-2, the IL2 may be administered in an adoptive immunotherapy method, together with isolated, lymphokine-activated lymphocytes, in a pharmaceutically acceptable carrier, where the lymphocytes are reactive to tumor when administered with the IL-2 to humans suffering from the tumor. This method is described more fully in U.S. Pat. No. 490,915 issued Sept. 1, 1987 (NTIS), and by S. Rosenberg et al., *New England Journal of Medicine* (1985), 313–1492.

In one specific application to animals, the succinylated IL-2 herein may be employed to enhance weight gain in livestock or domestic animals. The administration of an effective amount of human IL-2 to such animals, preferably for a prolonged period of time and at a dose of about $10^3$ to $10^5$ units/kg/day, is described more fully in U.S. application Ser. No. 778,370 filed September 20, 1985, now abandoned, the disclosure of which is incorporated herein by reference.

In another specific application to animals, the succinylated IL-2 herein may be employed to prevent and ameliorate in animals symptoms of stress and, in particular, of the malaise associated with livestock animals on feedlot, a symptomology commonly known as "shipping fever." The administration of an effective amount of human interleukin-2 to livestock, preferably cattle, to protect against such stress-induced syndromes is described more fully in U.S. application Ser. No. 778,371 filed Sept. 20, 1985, now abandoned, the disclosure of which is incorporated herein by reference.

Briefly, the regime of administration for shipping fever will depend on the conditions of shipment and the feedlot. It is preferred that administration be begun at least as early as arrival on the feedlot and be continued over a period of, for example, 1–8 or more days, as required either by multiple injections or by means of sustained release as described below. Total amounts in the range of $10^3$–$10^5$ units/kg/day are generally used.

For other livestock stress-related or respiratory distress syndromes, the regime and amounts administered will depend on the nature and size of the animal (e.g., pig, goat, sheep, etc.) and on the severity of the symptoms.

Preferably, the composition is administered for these veterinary purposes as a sustained release formulation. Such formulations are of considerable variety, as in understood by those skilled in the art. An exemplary composition for parenteral administration using substained release is an injectable microcapsule formulation that with a single injection will deliver recombinant human succinylated IL-2 at a controlled rate (0.07 to 7.0 mg/total dose) for a duration of 15 to 30 days for stress-induced syndromes, and at a controlled rate in the range of about $10^3$ to $10^5$ units/kg/day for enhancing weight gain. (Pure human IL-2 has a specific activity of about $3$–$6 \times 10^6$ U/mg, so the above total stress-induced syndromes dose converts to about $2 \times 10^5$ to about $4 \times 10^7$ units.)

The microcapsule formulation is a free-flowing powder consisting of spherical particles 20 to 100 $\mu$m in diameter that can be injected intramuscularly or subcutaneously with a conventional hypodermic needle, and the microcapsules consist of 0.5 to 5% human succinylated IL-2 encapsulated in poly (DL-lactide-co-glycolide) (DL-PLG) excipient, a biodegradable, biocompatible polyester. Alternative standard formulations for sustained release are also usable.

The dose and dosage regimen of the IL-2 will depend, for example, on the pharmacokinetics of the drug, the nature of the disease, the degree of succinylation, the characteristics of the IL-2, the patient and the patient's history. For example, different modified IL-2 proteins are expected to have different pharmacokinetic and therapeutic properties which are advantageous for different routes of adiministration. A long-acting drug might only be adiministered every 3–4 days, every week or once every two weeks. The clearance rate can be varied to give ultimate flexibility to fit the particular need of the patient by changing, e.g., the degree of succinylation. For example, the mono- and di-succinyulated IL-2 proteins have the same clearance rate as the unmodified IL-2. The more highly succinylated IL-2 proteins, however, have a faster clearance rate than the unmodified IL-2.

In the following examples, which illustrate the invention further, all parts and percentages are by weight unless otherwise noted, and all temperatures are in degrees Celsius.

EXAMPLE I

Preparation of Succinylated IL-2

A. Mono- and Di-Succinylated IL-2.

RP-HPLC purified recombinant des-alanyl, ser$_{125}$ IL-2 (where the cysteine at position 125 is replaced by serine and the N-terminal alanyl residue is deleted), prepared as described in U.S. Pat. Nos. 4,518,584 and 4,530,787, supra, was employed for this example. To 0.4 mg of this purified IL-2 in 1.0 ml buffer (0.1M sodium borate, pH 9; 0.1% SDS) was added 0.2 moles of succinic anhydride (in dimethylformamide) per mole of IL-2. After thorough mixing, the solutions were stirred at room temperature (23° C.) for 5 minutes. Then 0.2 moles of succinic anhydride per mole of IL-2 was added. This addition was repeated nine more times at 5-minute intervals. The reaction mixture was applied to a $1 \times 45$ cm Sephadex G-25 column (Pharmacia) to separate IL-2 and succinylated IL-2 species from low molecular weight species. The Sephadex G-25 column was run in 10 mM Na borate pH 9 containing no SDS and served also to remove most of the SDS from the reaction. The two species of succinylated IL-2 were separated from each other and from the unmodified IL-2 by applying the reaction mixture to a TSK-DEAE ion exchange HPLC column, with pH adjusted to 7. Then the purified pools were desalted and concentrated using Centricon 10 Microconcentrators.

B. Highly Succinylated IL-2.

To 5 mg/ml IL-2 solution containing 0.1M sodium borate, pH 9 and 0.1% SDS (the IL-2 being the post-diafiltered des-ala$_1$ser$_{125}$ IL-2 from the production process described above) was added with stirring at room temperature 10 moles of succinic anhydride (in DMF) per mole of IL-2 at 5-minute intervals, for a total of either three or six additions. Aliquots of the reaction mixture at various time points during the reaction were assayed for IL-2 biactivity (cell proliferation) by the methods generally described in Gillis, S., et al., *J. Immunol.*, 120, 2027–2032 (1978). The SDS was removed as described above, the pH was ajusted to 7.3, and the sample was concentrated to 0.7 mg/ml using Centricon 10 Microceoncentrators.

EXAMPLE II

Characterization of Succinylated IL-2 Species

A. Size Characterization of Modified IL-2 Products from Reactions with Varying Succinic Anhydride to IL-2 Molar Ratios.

SDS-PAGE (14%) of the products from the reaction described in Example I indicated that the two preparations of highly succinylated IL-2 showed slightly increased molecular weights over unmodified IL-2. The mono- and di-succinylated IL-2 species had molecular weights very near to that of unmodified IL-2.

B. Bioactivity of Succinylated IL-2 as a Function of the Extent of Modification.

Fractions from the aforementioned elutions of highly succinylated IL-2 reaction of Example IB were assayed by the IL-2 cell proliferation bioassay described in Example I. The results show that all IL-2 fractions are bioactive. Large variations in specific bioactivity of IL-2 cause the bioactivity of the succinylated IL-2 to be about ±30% of the bioactivity of the unmodified IL-2.

C. Solubility of Succinylated IL-2 Compared to Unmodified IL-2.

After the reaction and subsequent Sephadex G-25 chromatography resulting in SDS removal, the pH of all the IL-2 preparations was lowered to 6.5–7. The unmodified IL-2 in low SDS precipitated at pH 5–7. The mono-succinylated IL-2 exhibited improved solubility without added solubilizing agents, but storage at 4° C. for three days or physical agitation at room temperature caused visible precipitation of the mono-succinylated IL-2. However, the highly succinylated IL-2 was completely soluble at 0.7 mg/ml and the solution was stable over weeks at 4° C. The solubility of the di-succinylated was not determined.

D. Pharmacokinetics of Succinylated IL-2 Compared to Unmodified IL-2.

1. Mono- and Di-Succinylated IL-2.

Pharmacokinetic data of unmodified IL-2 and the mono- and di-succinylated IL-2 were obtained after intravenous administration of 12.5 μg of protein in D5W (5% dextrose in water) in each mouse in a total of 8 mice, four per group.

Each mouse from two groups of four female balb/c mice was injected with one of the three samples into the tail vein and all were bled retro-orbitally at 1.5 min. At various later times after injection 100 μl blood samples were removed retro-orbitally into heparinized capillary tubes. Plasma was prepared immediately by centrifugation (1 min.) and an aliquot was diluted into assay medium for bioassay as described in Example I.

The results indicated that, within experimental error, plasma clearance of mono- and di-succinylated IL-2 was the same as that of unmodified IL-2.

2. Highly Succinylated IL-2

Three cannulated male Sprague-Dawley rats were injected intravenously with the succinylated IL-2 (two rats with unmodified IL2). The rats were bled from the cannula at each time point and plasma was prepared and diluted into medium for bioassay as described above. Highly succinylated IL-2 was found to clear faster than unmodified IL-2.

In summary, the present invention is seen to provide a succinylated IL-2 and pharmaceutical composition containing such IL-2, wherein a biologically active specific IL-2 selectively conjugated to one or more succinyl moieties and thereby made soluble or more soluble in an aqueous medium at physiological pH is dissolved in such medium. The conjugation serves not only to solubilize the normally hydrophobic water-insoluble protein in water at pH 6–8, but also in some cases alters its physiological half-life. Without the conjugation, the IL-2 must e solubilized by addition of solubilizing agents such as detergents or denaturants, by raising the pH in combination with addition of a stabilizer, or by lowering the pH.

The foregoing written specification is considered to be sufficient to enable one skilled in the art to practice the invention. Indeed, various modifications of the above-described modes for carrying out the invention which are obvious to those skilled in the field of pharmaceutical formulation or related fields are intended to be within the scope of the following claims.

What is claimed is:

1. A biologically active, conjugated, recombinant interleukin2 that is covalently and selectively conjugated to one or more succinyl moieties, wherein said interleukin-2 in its unconjugated form is hydrophobic and insoluble or not readily soluble in water or an aqueous carrier medium under ambient conditions of room temperature and atmospheric pressure at a pH of between about 6 and 8 in the absence of a solubilizing agent.

2. A pharmaceutical composition comprising a non-toxic, inert, pharmaceutically acceptable aqueous carrier medium in which is dissolved the interleukin-2 of claim 1.

3. The composition of claim 2 wherein the interleukin-2 is conjugated to one or two succinyl moieties.

4. The composition of claim 2 wherein the interleukin 2 is conjugated to more than two succinyl moieties.

5. The composition of claim 2 wherein the medium is at a pH of about 5–8 and contains a buffer.

6. The composition of claim 2 wherein the medium is at a pH of about 6.8–7.8 and contains a buffer.

7. The composition of claim 2 wherein the interleukin-2 is a recombinant interleukin-2 from a human source.

8. The composition of claim 7 wherein the interleukin-2 is an interleukin-2 mutein.

9. The composition of claim 8 wherein said mutein has the amino acid(s) that are at position 104 or 125 or positions 104 and 125 in the native protein substituted with a neutral amino acid.

10. The composition of claim 9 wherein said mutein is $ser_{125}IL$-2, des-ala-$_1ser_{125}IL$-2, des-ala$_1$ala-$_{104}IL$-2, or des-ala$_1$ala$_{104}$ser$_{125}IL$-2.

11. A process for preparing a biologically active, succinylated interleukin-2 comprising:
   (a) reacting succinic anhydride with biologically active, normally hydrophobic, recombinant interleukin-2 that before succinylation is insoluble or not readily soluble in water or an aqueous medium under ambient conditions of room temperature and atmospheric pressure at a pH of between about 6 and 8; and
   (b) isolating the succinylated interleukin-2.

12. A process for preparing a pharmaceutical composition comprising:
   (a) reacting succinic anhydride with biologically active, normally hydrophobic, recombinant interleukin-2 that before succinylated is insoluble or not readily soluble in water or an aqueous medium under ambient conditions of room temperature and atmospheric pressure at a pH of between about 6 and 8;
   (b) isolating the succinylated interleukin-2; and
   (c) formulating said succinylated interleukin-2 in a non-toxic, inert, pharmaceutically acceptable aqueous carrier medium.

13. The process of claim 11 wherein in step (a) a total of at least 2 moles of succinic anhydride is employed per mole of interleukin-2.

14. The process of claim 112 wherein in step (a) a total of at least 2 moles of succinic anhydride is employed per mole of interleukin-2.

15. The process of claim 12 wherein the succinylated interleukin-2 is formulated at a pH of 6-8 and the interleukin-2 is from a human source.

16. The process of claim 15 wherein said interleukin-2 is recombinant interleukin-2.

17. The composition of claim 1 that is formulated as an injectable microcapsule that with a single injection delivers the IL-2 in a total dose of about $2 \times 10^5$ to about $4 \times 10^7$ units for 15 to 30 days.

18. The composition of claim 1 that is formulated as an injectable microcapsule that with a single injection delivers the IL-2 in an amount of about $10^3$ to $10^2$ units/kg/day.

19. The composition of claim 1 that is formulated as an injectable microcapsule comprising a powder of particles 20 to 100 μm in diameter that comprise 0.5 to 5% of said IL-2 encapsulated in a biodegrabable, biocompatible polyester.

20. The composition of claim 19 wherein the polyester is poly(DL-lactide-co-glycolide).

* * * * *